United States Patent [19]

Dettbarn et al.

[11] 4,400,171
[45] Aug. 23, 1983

[54] NEEDLE-LESS INJECTION INSTRUMENT

[75] Inventors: Hans-Jürgen Dettbarn, Marburg/Lahn; Josef Zimmermann, Sulzbach, both of Fed. Rep. of Germany

[73] Assignee: Hoechst Aktiengesellschaft, Frankfurt am Main, Fed. Rep. of Germany

[21] Appl. No.: 368,217

[22] Filed: Apr. 14, 1982

[30] Foreign Application Priority Data

Apr. 16, 1981 [DE] Fed. Rep. of Germany ....... 3115374

[51] Int. Cl.³ ............................................. A61M 5/30
[52] U.S. Cl. ..................................................... 604/68
[58] Field of Search ................................... 604/68–72, 604/131, 140, 148, 149, 150, 181

[56] References Cited

U.S. PATENT DOCUMENTS

| | | | |
|---|---|---|---|
| 2,671,347 | 3/1954 | Scherer | 604/68 |
| 2,816,544 | 12/1957 | Scherer et al. | 604/68 |
| 2,928,390 | 3/1960 | Venditty et al. | 604/71 |
| 4,266,541 | 5/1981 | Landau | 604/68 |

Primary Examiner—John D. Yasko
Attorney, Agent, or Firm—Curtis, Morris & Safford

[57] ABSTRACT

In this injection instrument, the piston pump (A) is connected to a drive motor (B), of which the working piston (5), supported on a working spring (2), is arranged displaceably in a cylindrical bore (6) of the motor housing (1). A pressure chamber (7) which has supply devices (3, 8) and discharge devices for the pressure medium is formed in the bore (6). The working spring (2) is held in a tensioned position by a pawl (10) supported by a bolt (13), the bolt (13) being supported on an operating element (C).

So that injection can be initiated only when the nozzle (23) is pressed onto the subject, the bolt (13) is connected rigidly to the operating element (C), and its free end is arranged displaceably in the motor housing (1).

3 Claims, 5 Drawing Figures

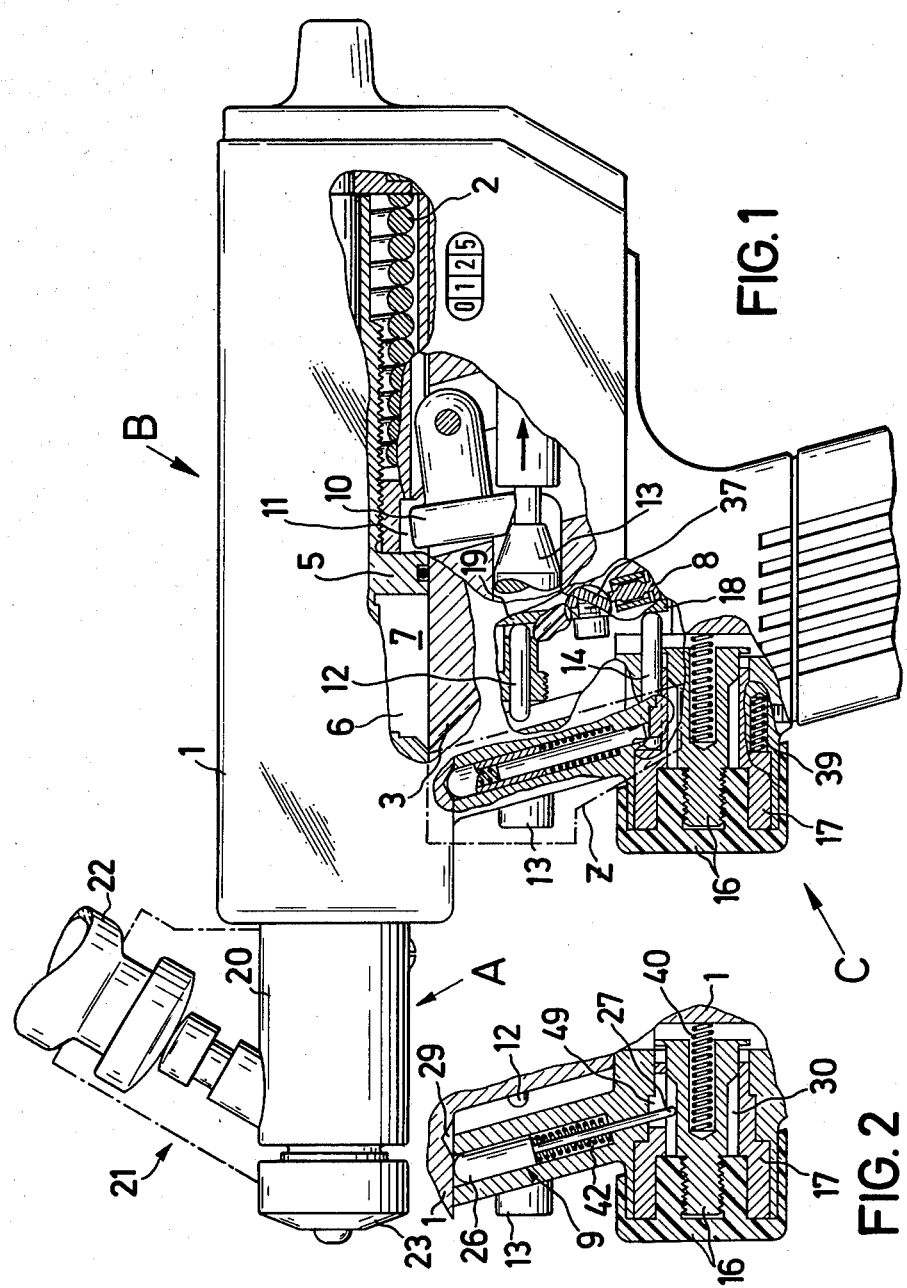

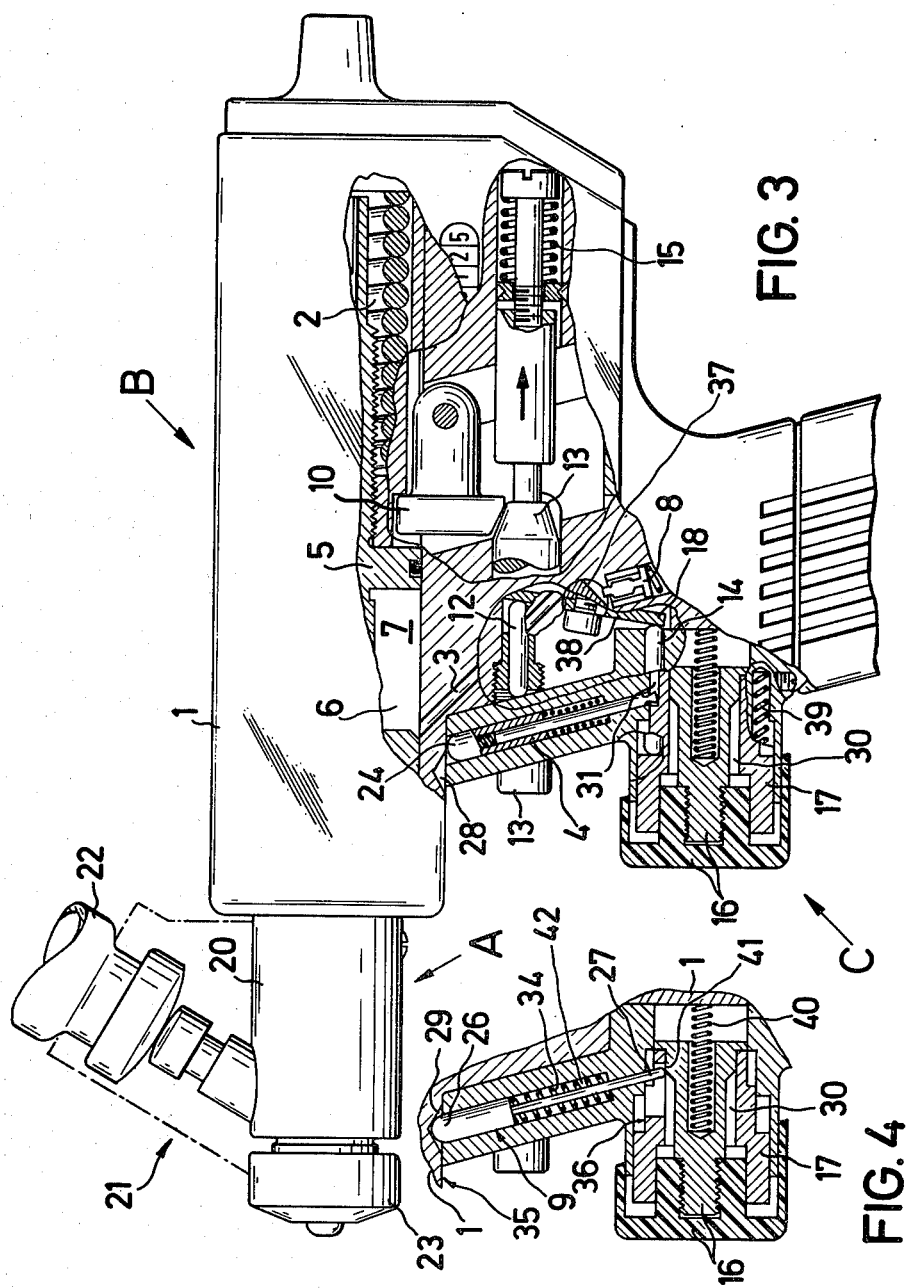

NEEDLE-LESS INJECTION INSTRUMENT

The invention relates to a needle-less injection instrument with a piston pump for the medium to be injected, which is connected to a drive motor, of which the working piston, supported on a working spring, is arranged displaceably in a cylindrical bore of the motor housing, there being formed in the cylindrical bore a pressure chamber for receiving a pressure medium to tension the working spring, which has supply and discharge devices for the pressure medium, the working spring being held in a tensioned position by a pawl supported by a bolt, the bolt being supported on an operating element.

A needle-less injection instrument of the type mentioned is known from German Pat. No. 1,080,267. The working springs tensioned by hydraulic fluid are held in a tensioned position by a pawl supported by a bolt. The bolt is supported on a trigger. Located in the servicing device and supply device for the hydraulic fluid is a solenoid valve, the circuit of which is connected to an electrical switch, the contacts of which are actuated by means of a valve cam for the medium to be injected. A disadvantage of this is that the compressed springs have to be held in position by the hydraulic fluid and that an unintentional release of the pawl and consequently shooting of the injection as a result of actuation of the trigger is possible at any time.

The invention is intended to remedy this. The invention, as defined in the claims, achieves the object by an arrangement wherein the operating element is connected rigidly to the bolt and the bolt is arranged displaceably in the motor housing. The operating element consists of a spring-loaded operating knob which is engaged with a spring-loaded sleeve arranged concentrically to the operating knob; a telescopically sprung plunger being assigned to the sleeve and a rigid plunger being assigned to the operating knob, the two plungers being guided in appropriate bores in the operating element and being supported by springs, and the sleeves of the operating knob and the motor housing being provided with recesses into which the plungers engage alternately, a pin for actuating the supply device for the pressure medium being assigned to the sleeve in an axial direction. The telescopically sprung plunger can have stops for limiting its deflection.

The advantages achieved by means of the invention are to be seen essentially in the fact that it is ensured that injection can be initiated only when the nozzle of the injection instrument is pressed onto the subject to be injected. A further advantage is that, during the operation to tension the working spring, it is not possible to initiate injection and, conversely, it is not possible to tension the working spring during injection.

The invention is explained in more detail below with reference to drawings which illustrate only one form of construction and in which:

FIG. 1 shows a side view of the injection instrument, partially in section and in sections along various planes, in the virtually cocked state; the operating element C is still disengaged, the operating knob is pressed and the telescopic plunger is shown in section;

FIG. 2 shows the operating element still disengaged, with the operating knob pressed and the rigid plunger shown in section;

FIG. 3 shows a side view of the injection instrument, partially in section and in sections along various planes, in the cocked state; the operating element (C) rests against the motor housing; the operating knob is disengaged;

FIG. 4 shows the operating element in section;

Figure 5:
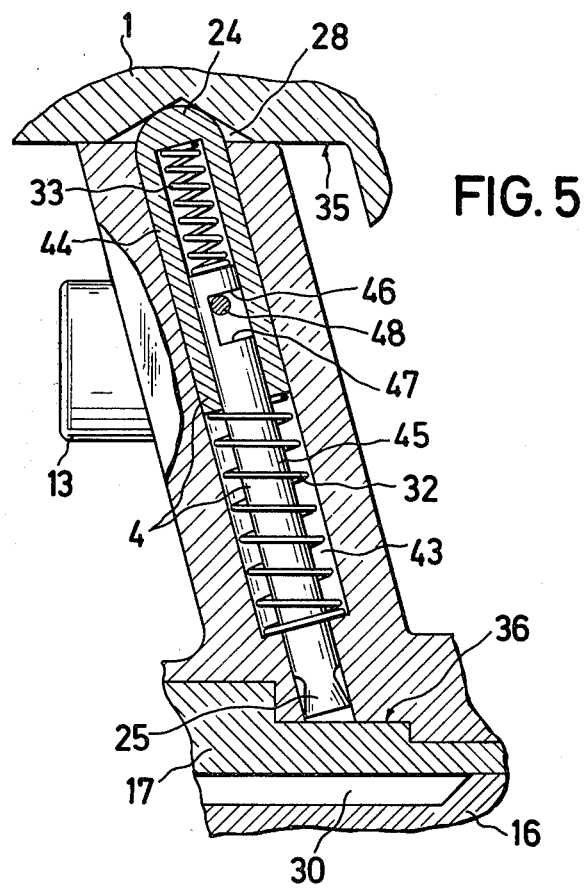
FIG. 5 shows the detail "Z" of FIG. 1.

The needle-less injection instrument consists essentially of a piston pump (A) for the medium to be injected, which is connected to a drive motor (B). The housing (20) of the piston pump (A) carries a device (21) for receiving a vessel (22) for the medium to be injected, and the nozzle (23). The working piston (5) of the drive motor (B) is arranged displaceably in a cylindrical bore (6) of the motor housing (1). The working spring (2) of the working piston (5) is tensioned by means of a pressure medium, for example hydraulic fluid or gas, which is supplied via an inlet valve (8) and via a channel (3) to the pressure chamber (7) in the cylindrical bore (6). The operating element (C) consists essentially of an operating knob (16), a sleeve (17) arranged concentrically to the operating knob, a rigid plunger (9) and a telescopically sprung plunger (4). The plungers (9) and (4) are mounted resiliently in bores (42) and (43) of the operating element, for example a grip. Recesses (28, 29) and (30, 31) are located in the motor housing (1) and the sleeve (17) respectively, and the operating knob (16). The ends (26) and (27) of the plunger (9) are received by the recesses (29) and (30) respectively, and the ends (24) and (25) of the plunger (4) are received by the recesses (28) and (31) respectively. The plungers engage alternately into the recesses. Before the working spring (2) is tensioned, the guide bore (43) of the resilient plunger (4) is aligned with the recess (28) in the motor housing, so that the resilient plunger (4) is pressed by the spring (32) into the recess (28). The lower end (25) of the plunger (4) is lifted until the sleeve (17) can slide to the rear when the operating knob (16) is pressed. The resilient plunger (4) consists of a sleeve (44), a ram (45) sliding therein and a spring (33). The deflection of the plunger (4) is limited by stops (46), and (47) and (48) on the ram (45) and sleeve (44) respectively.

The guide bore (42) of the rigid plunger (9) is not aligned with the recess (29) in the motor housing (1) before the working spring (2) is tensioned, so that the upper end (26) of the plunger (9) rests against the plane face (35) of the motor housing and the lower end (27) of the plunger (9) projects through a perforation (49) in the sleeve (17) into the recess (30) of the operating knob (16).

When the operating knob (16) is pressed, the sleeve (17) is also pushed back. At the same time, the sleeve (17) presses on the plunger (14) and the latter presses, in turn, on the end (18) of the lever (38); the inlet valve (8) is opened, the working spring (2) is tensioned, the recess (11) comes to rest opposite the pawl (10), and the bolt (13) is drawn in the direction of the arrow by the spring (15), as is the operating element (C) connected to the bolt (13). During the time when the operating element (C) slides back, the plunger (12) is pressed and engages on the end (19) of the lever (38) of the control shaft (37), and consequently, the outlet valve is opened, so that the pressure medium can leave the pressure chamber (7). The upper end (24) of the resilient plunger (4) is pushed out of the recess (28), the upper end (24) of the plunger (4) being pressed by the springs (32) and (33) against the face (35) of the motor housing, and the lower end (25) of the plunger (4) being pressed by the spring (33) onto the face (36) of the sleeve (17). At the same time, the rigid plunger (9) is pressed into the recess (29) in the motor housing (1) by the spring (34), the lower end (27) being disengaged from the recess (30). When the operating knob (16) is released, the sleeve (17) is pushed into the initial position by springs (39) and the operating knob (16) is pushed into the initial position by the spring (40). At the same time, the lower end (25) of the resilient plunger (4) slips into the recess (31) of the sleeve (17) and prevents the sleeve (17) from being pushed back again and, consequently, the inlet valve (8) from being opened again, as long as the vaccinating gun is cocked (FIG. 3). When the operating knob (16) slides forward, the shoulder (41) of the lower end (27) of the plunger (9) comes to rest opposite the latter, so that displacement of the operating element (C) and consequently, initiation of injection become possible only when the operating knob (16) is pressed again (FIG. 4).

We claim:

1. A needle-less injection instrument with a piston pump for the medium to be injected, which is connected to a drive motor, of which the working piston, supported on a working spring, is arranged displaceably in a cylindrical bore of the motor housing, there being formed in the cylindrical bore a pressure chamber for receiving a pressure medium to tension the working spring, which has supply and discharge devices for the pressure medium, the working spring being held in a tensioned position by a pawl supported by a bolt, and the bolt being supported on an operating element, wherein the operating element C is connected rigidly to the bolt (13), and the bolt (13) is arranged displaceably in the motor housing (1).

2. The needle-less injection instrument as claimed in claim 1, wherein the operating element C consists of a spring-loaded operating knob (16) which is engaged with a spring-loaded sleeve (17) arranged concentrically to the operating knob (16), a telescopically sprung plunger (4) being assigned to the sleeve (17) and a rigid plunger (9) being assigned to the operating knob (16), the two plungers being guided in appropriate bores (42, 43) in the operating element C and being supported by springs (32, 33, 34), and the sleeve (17), operating knob (16) and motor housing (1) being provided with recesses (28, 29, 30, 31) into which the plungers (4, 9) engage alternately, and a plunger (14) for actuating the supply device for the pressure medium being assigned to the sleeve (17) in an axial direction.

3. The needle-less injection instrument as claimed in claim 2, wherein the telescopically sprung plunger (4) has stops (46, 47, 48) for limiting its deflection.

* * * * *